United States Patent
Boyer

(10) Patent No.: US 12,296,073 B2
(45) Date of Patent: May 13, 2025

(54) WAX MELTER APPARATUS WITH A WAX REMOVAL MECHANISM

(71) Applicant: Relm LLC, Castle Rock, CO (US)

(72) Inventor: Taylor Boyer, Castle Rock, CO (US)

(73) Assignee: Relm LLC, Castle Rock, CO (US)

( * ) Notice: Subject to any disclaimer, the term of this patent is extended or adjusted under 35 U.S.C. 154(b) by 0 days.

(21) Appl. No.: 18/601,600

(22) Filed: Mar. 11, 2024

(65) Prior Publication Data

US 2024/0299608 A1 Sep. 12, 2024

Related U.S. Application Data

(60) Provisional application No. 63/489,601, filed on Mar. 10, 2023.

(51) Int. Cl.
*A61L 9/03* (2006.01)
*H05B 3/74* (2006.01)

(52) U.S. Cl.
CPC . *A61L 9/03* (2013.01); *H05B 3/74* (2013.01)

(58) Field of Classification Search
None
See application file for complete search history.

(56) References Cited

U.S. PATENT DOCUMENTS

| | | | | |
|---|---|---|---|---|
| D735,255 | S | * | 7/2015 | Sickinger .................. D15/144.2 |
| D913,471 | S | * | 3/2021 | Walter .......................... D23/366 |
| 2016/0346419 | A1 | * | 12/2016 | Gasper ...................... H05B 3/24 |
| 2017/0238364 | A1 | * | 8/2017 | Belongia .................... A61L 9/03 |
| | | | | 219/422 |
| 2018/0071424 | A1 | * | 3/2018 | Kong ........................ A61L 9/03 |
| 2020/0205235 | A1 | * | 6/2020 | Anderson ............ H05B 3/0071 |
| 2021/0300158 | A1 | * | 9/2021 | Yahnite ...................... A61L 9/03 |
| 2022/0401609 | A1 | * | 12/2022 | Wynn ........................ A61L 9/03 |

FOREIGN PATENT DOCUMENTS

GB 2527346 A * 12/2015 ............... A61L 2/00

OTHER PUBLICATIONS

Amazon.com: Happy Wax Mod Wax Melt Warmer, 2025 [retrieved Jan. 3, 2025]. Retrieved from the Internet: <URL: https://www.amazon.com/Happy-Wax-Warmer-Timer-Scented/dp/B0BCM3F4DG/>. (Year: 2025).*

* cited by examiner

*Primary Examiner* — John J Norton
(74) *Attorney, Agent, or Firm* — Hall Estill Law Firm

(57) ABSTRACT

A wax melter apparatus. The wax melter apparatus includes a housing and a heating element to provide heat to melt wax. The wax melter apparatus also includes a flexible dish supported by the housing, the flexible dish receives the wax to be melted and can be distorted to allow cooled and hardened wax to be easily removed.

22 Claims, 8 Drawing Sheets

WAX MELTER APPARATUS WITH A WAX REMOVAL MECHANISM

CROSS-REFERENCE TO RELATED APPLICATIONS

The present application is a conversion of U.S. Provisional application having U.S. Ser. No. 63/489,601, filed Mar. 10, 2023, which claims the benefit under 35 U.S.C. 119(e). The disclosure of which is hereby expressly incorporated herein by reference.

STATEMENT REGARDING FEDERALLY SPONSORED RESEARCH OR DEVELOPMENT

Not applicable.

BACKGROUND OF THE DISCLOSURE

1. Field of the Invention

The present disclosure generally relates generally to a wax melter apparatus with various unique features such as a mechanism to remove the leftover wax.

2. Description of the Related Art

Aromatherapy wax melters are widely used in homes to create a pleasant scent in a particular living space. However, traditional wax melters suffer from two common problems. Firstly, they lack IoT (internet of things) connectivity, which is now a standard feature in most household appliances. Secondly, there is a problem disposing of the wax. If they attempt to dispose of the wax while it is hot, they run the risk of subjecting themselves to potential burns. If they wait for the wax to cool, they will have to scrape the dry wax out of the reservoir, which can create messes and leaves unwanted residue in the device.

Accordingly, there is a need for a wax melter apparatus that includes a mechanism to remove the leftover wax from the wax melter.

SUMMARY OF THE DISCLOSURE

The present disclosure is directed to a wax melter apparatus. The wax melter apparatus includes a housing and a heating element to provide heat to melt wax. The wax melter apparatus also includes a flexible dish supported by the housing, the flexible dish receives the wax to be melted and can be distorted to allow cooled and hardened wax to be easily removed.

DETAILED DESCRIPTION OF THE DISCLOSURE

Figure 1:
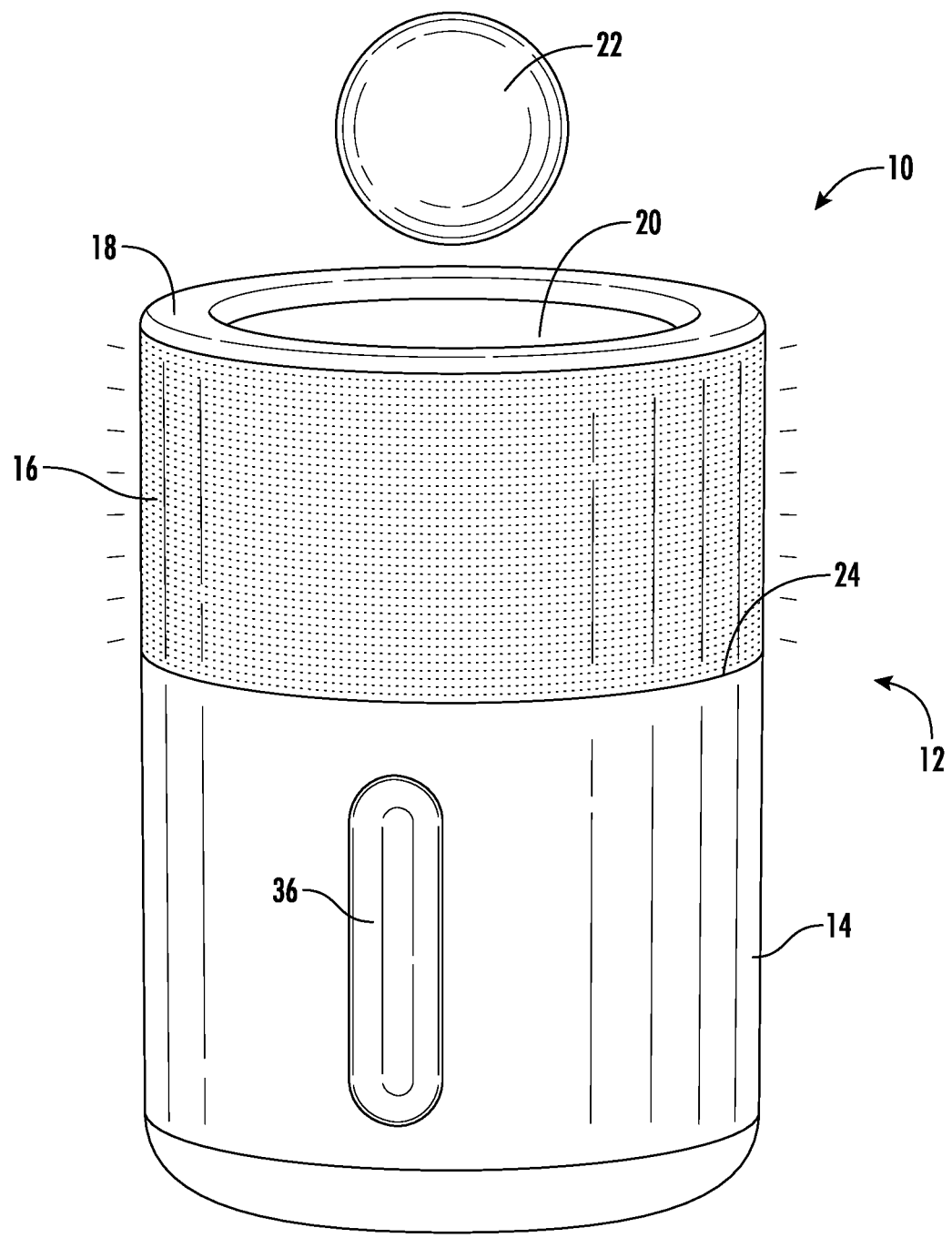
FIG. 1 is a perspective view of one embodiment of a wax melter apparatus constructed in accordance with the present disclosure.
Figure 2:
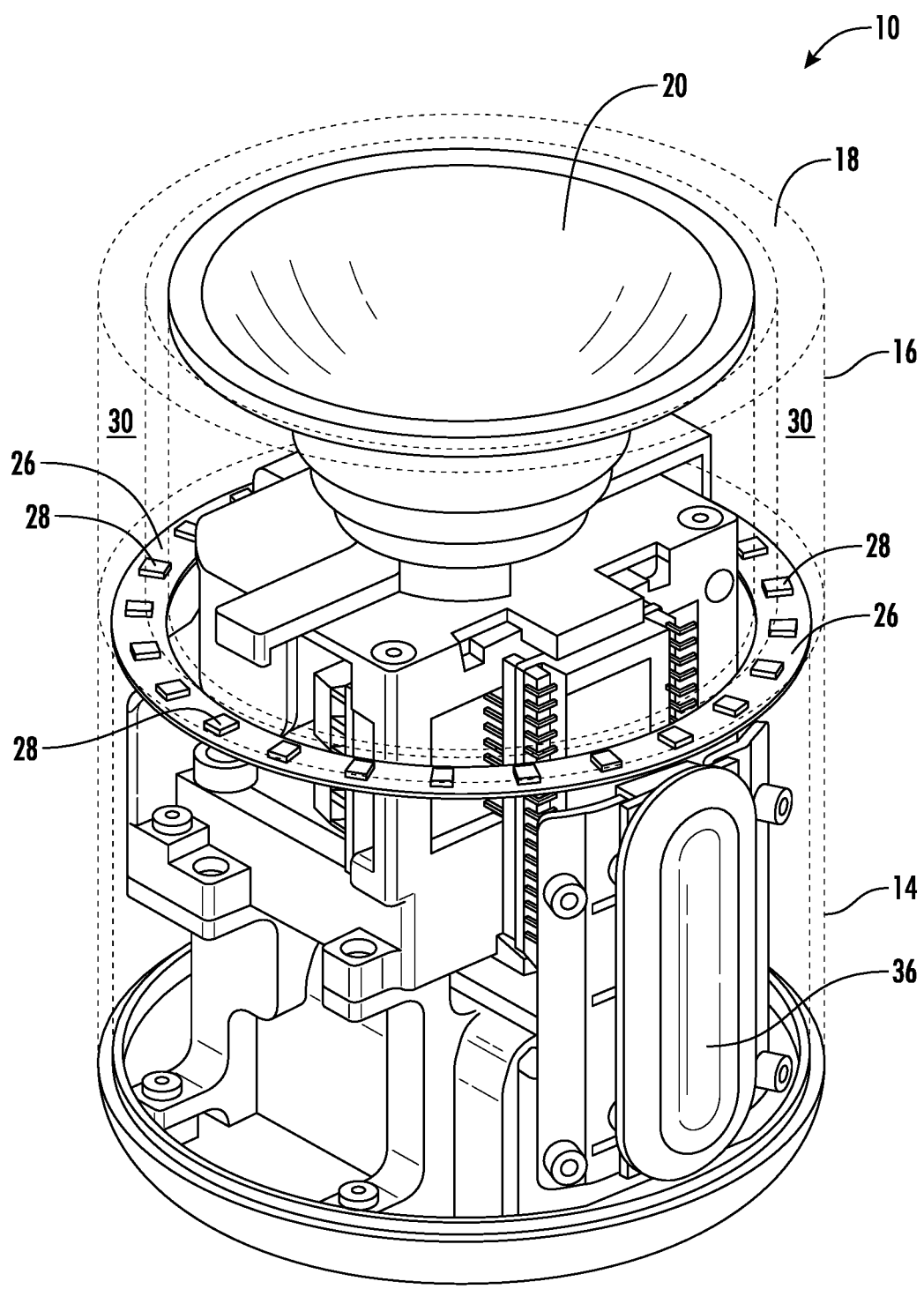
FIG. 2 is an internal perspective view of the wax melter apparatus constructed in accordance with the present disclosure.
Figure 3:
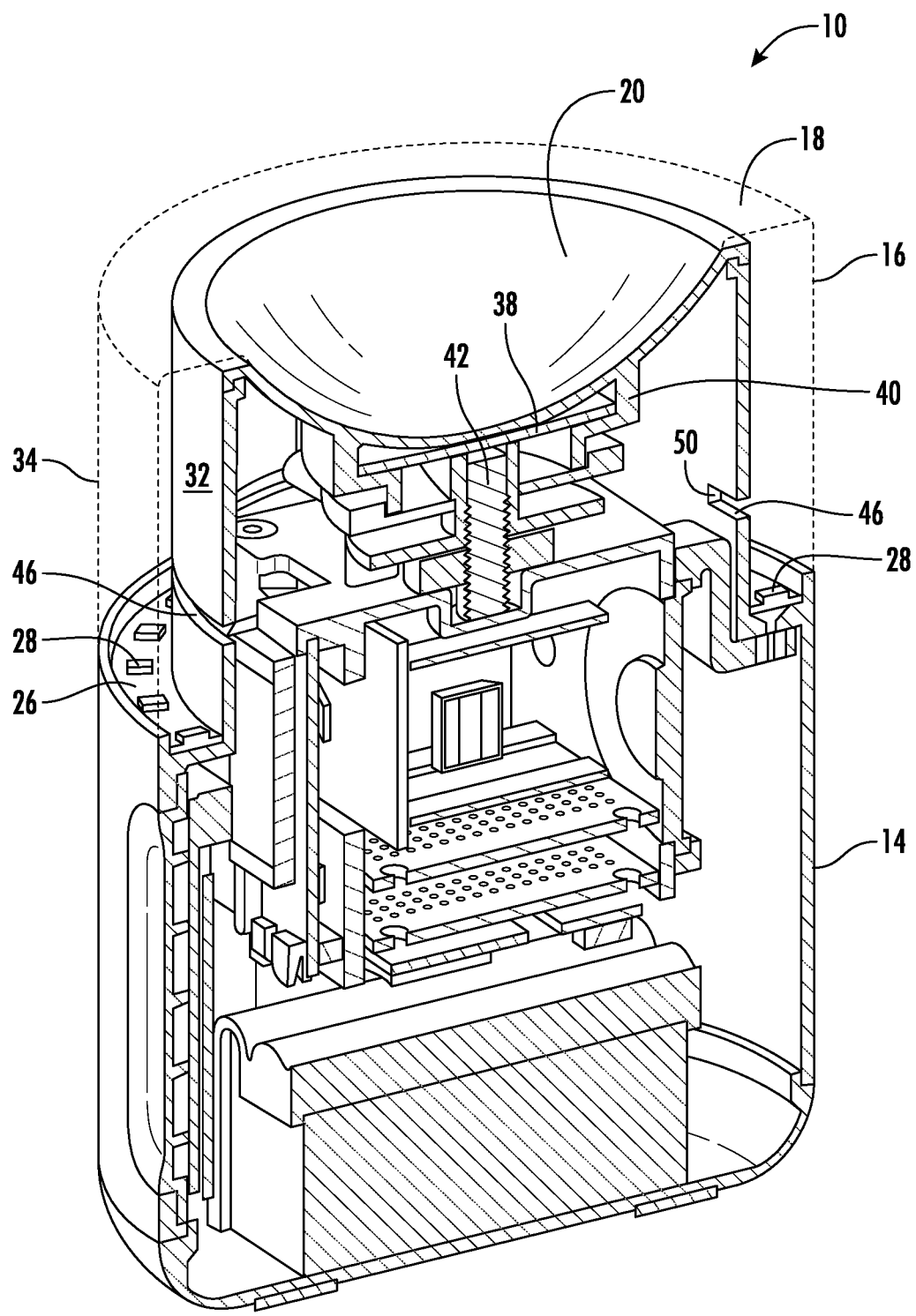
FIG. 3 is an internal perspective, cross-sectional view of the wax melter apparatus constructed in accordance with the present disclosure.

Referring now to FIGS. 1-3, shown therein is a wax melter apparatus 10 having unique features such as a mechanism to easily eject and remove leftover wax, LED capabilities, light dimming capabilities, etc. The wax melter apparatus 10 will also be designed wherein certain features can be operated manually, operated by voice command and/or operated via a mobile application downloaded to a consumer device such as a mobile phone, tablet, computer, etc. The wax melter apparatus 10 can include a housing 12 that can be made up of a base portion 14 and an upper portion 16. The housing 12 encapsulates various components of the wax melter apparatus 10 that make it operational. A top side 18 of the upper portion 16 can include a flexible dish 20 where the wax 22 can be deposited therein. The flexible dish 20 can be comprised of any material capable of handling the operating temperatures required for the wax melter apparatus 10 and still have a flexible quality to allow proper functionality of the wax melter apparatus 10. In one exemplary embodiment, the flexible dish 20 can be made of a silicon containing material.

The base portion 14 can include an upper ring end 24 that can support the upper portion 16 of the housing 12. The upper ring end 24 can also support an LED ring 26 with multiple LEDs 28 that can project light up into a sleeve cavity 30 of the upper portion 16 of the housing 12. The sleeve cavity 30 can be defined by an inner sleeve 32 and an outer sleeve 34. The outer sleeve 34 can be transparent to permit the light from the LED ring 26 to be seen. The LED ring 26 can be operated to be multiple different colors and be designed to be dimmable to allow a user to achieve a desired level of mood lighting. The base portion 14 can have a dimmer pad 36 disposed on a side to provide a mechanism for a user to control the brightness of the LED ring 26 and is used to be able to turn the LED ring 26 on and off. The wax melter apparatus 10 includes all necessary hardware and software to support the operability of the LED ring 26 and the dimmer pad 36.

The wax melter apparatus 10 can also include a heating element 38 that is disposed adjacent to the flexible dish 20 to heat and melt the wax 22 put into the flexible dish 20. The heating element 38 can be supported by an ejection apparatus 40, which can be forced to engage and deform the flexible dish 20 to disengage wax 22 that has cooled and hardened in the flexible dish 20 to easily remove the cooled and hardened chunk of wax. The ejection apparatus 40 can be directly attached to the flexible dish 20 or it can be supported by other parts of the wax melter apparatus 10 and be positioned adjacent to a bottom side of the flexible dish 20. The wax melter apparatus 10 can include any and all necessary software and hardware to facilitate operation of the heating element 38. The wax melter apparatus 10 can include a wax life preservation feature that causes the heating element 38 to toggle between different temperatures, which causes the wax life to last longer and reintroduce scent from the wax into living spaces.

A mobile application can be downloaded to a consumer device to control various aspects of the wax melter apparatus 10. The functions of the wax melter apparatus 10 that can be controlled via the mobile application can include, but is not limited to, powering the wax melter apparatus 10 on and off, the brightness of the LED ring 26, initiating the wax life preservation feature, a wax life monitor, scheduling when the wax melter apparatus 10 will be turned on, and connectivity and setup of the wax melter apparatus 10. The wax melter apparatus 10 includes all necessary software and hardware commonly known to those of ordinary skill in the art for operation of various devices. For example, the wax melter apparatus 10 can include a power source, a power converter, a wifi chip, Bluetooth capabilities, communication interface, microphone, lighting unit, printed circuit board (PCB), processor(s), wiring, memory, etc.

Figure 4A:
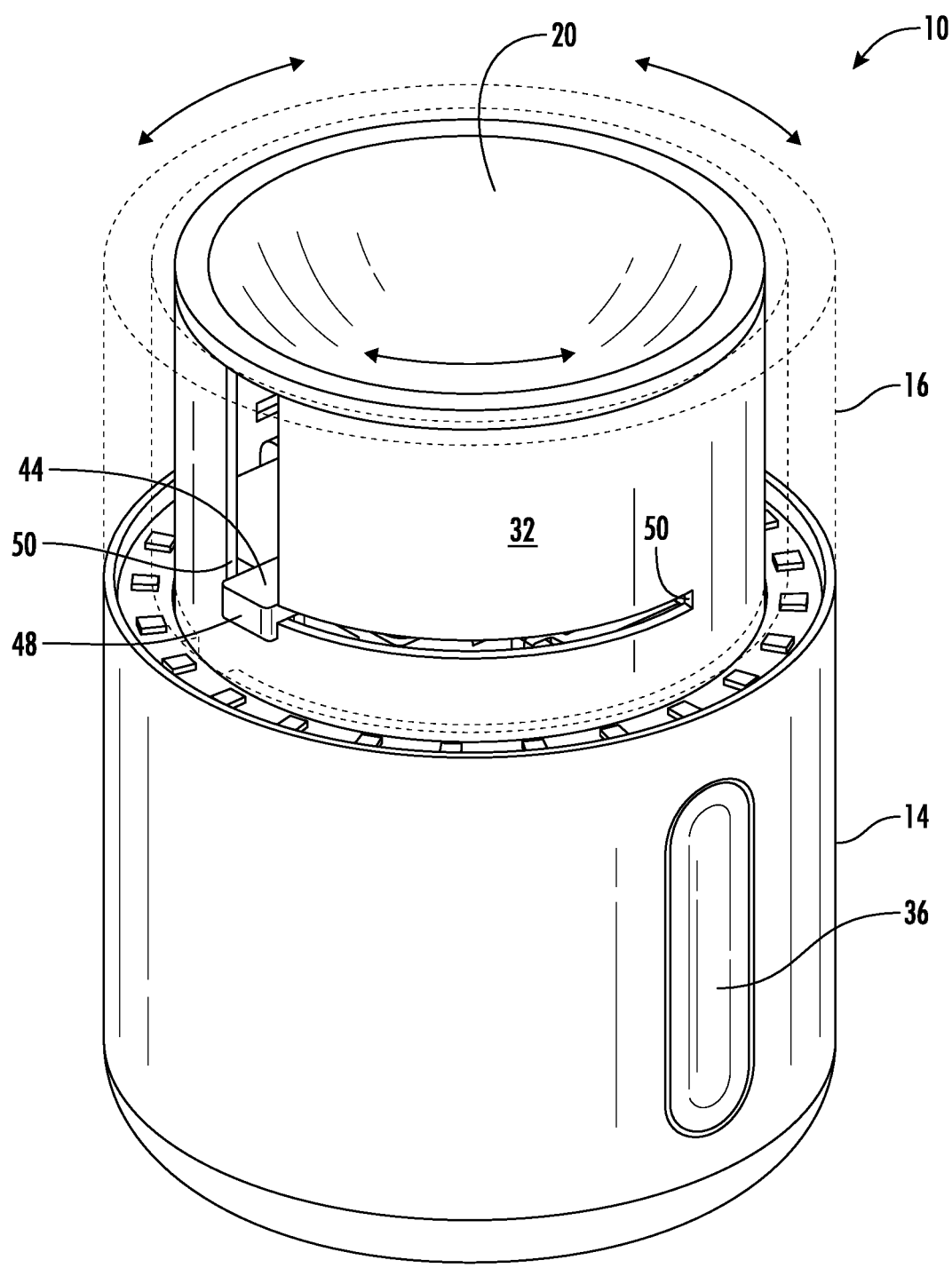
FIGS. 4A-4C are various views of one embodiment of the wax melter apparatus constructed in accordance with the present disclosure.
Figure 4B:
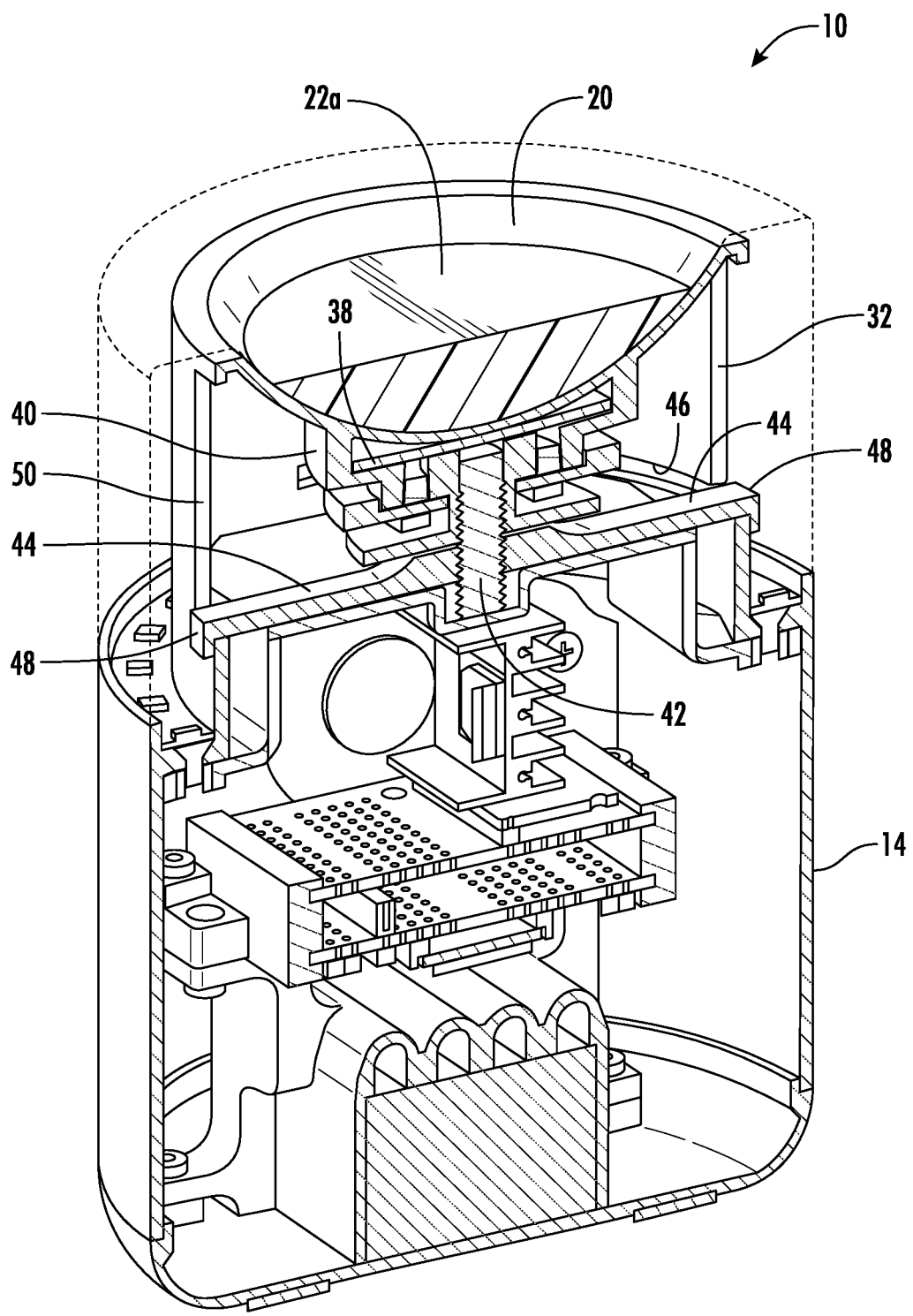
Figure 4C:
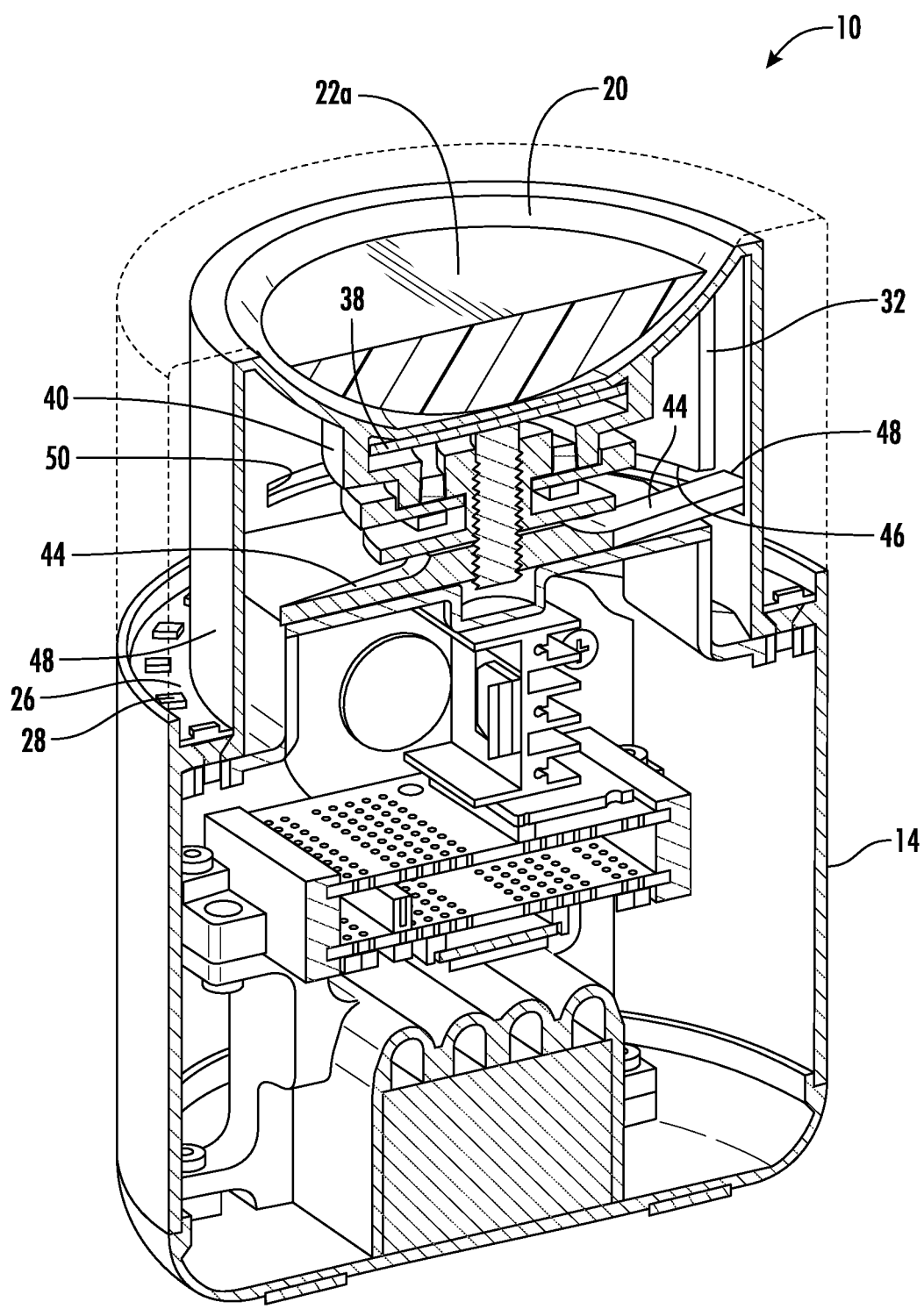

In one embodiment shown in FIGS. 4A-4C, the wax removal mechanism can include a rod member 42 disposed vertically within the ejection apparatus 40 and an arm member 44 that cooperates and is threadably engaged with the rod member 42 to drive the rod member 42 upwards to cause the heating element 38 to be forced into the flexible dish 20 to cause the flexible dish 20 to deform and allow the cooled and hardened wax 22a to become unstuck to the flexible dish 20. The rod member 42 can be threaded into an opening 45 disposed in the middle of the arm member 44. In this embodiment the upper portion 16 of the housing 12 is rotatably disposed on the base portion 14. The inner sleeve 32 of the upper portion 16 can have horizontal slats 46 disposed therein. The ends 48 of the arm member 44 can extend through the horizontal slats 46 such that when the terminal ends 50 of the vertical slats 46 engage the ends 48 of the arm member 44, the arm member 44 is rotated. The terminal ends 50 of the vertical slats 46 are caused to engage the ends 48 of the arm member 44 by rotating the upper portion 16 of the housing 12 relative to the base portion 14.

When the arm member 44 is rotated one direction, the rod member 42 is driven upwards causing the heating element 38 to engage the flexible dish 20 and distort the shape of the flexible dish 20. The distortion of the flexible dish 20 causes the cooled and hardened wax 22a to be unstuck from the flexible dish 20. When the arm member 44 is rotated back the other way, the rod member 42 is rotated downwards and the flexible dish 20 is allowed to move back to its resting shape. The rod member 42 is driven upwards or downwards by the rotation of the arm member 44 because the rod member 42 can have groove running down its length that engages a tongue running vertically down the ejection apparatus 40 to prevent rotation of the rod member 42 when the arm member 44 is rotated. This tongue and groove relationship translates rotation of the arm member 44 to linear movement of the rod member 42 due to the threaded relationship between the rod member 42 and the arm member 44.

Figure 5A:
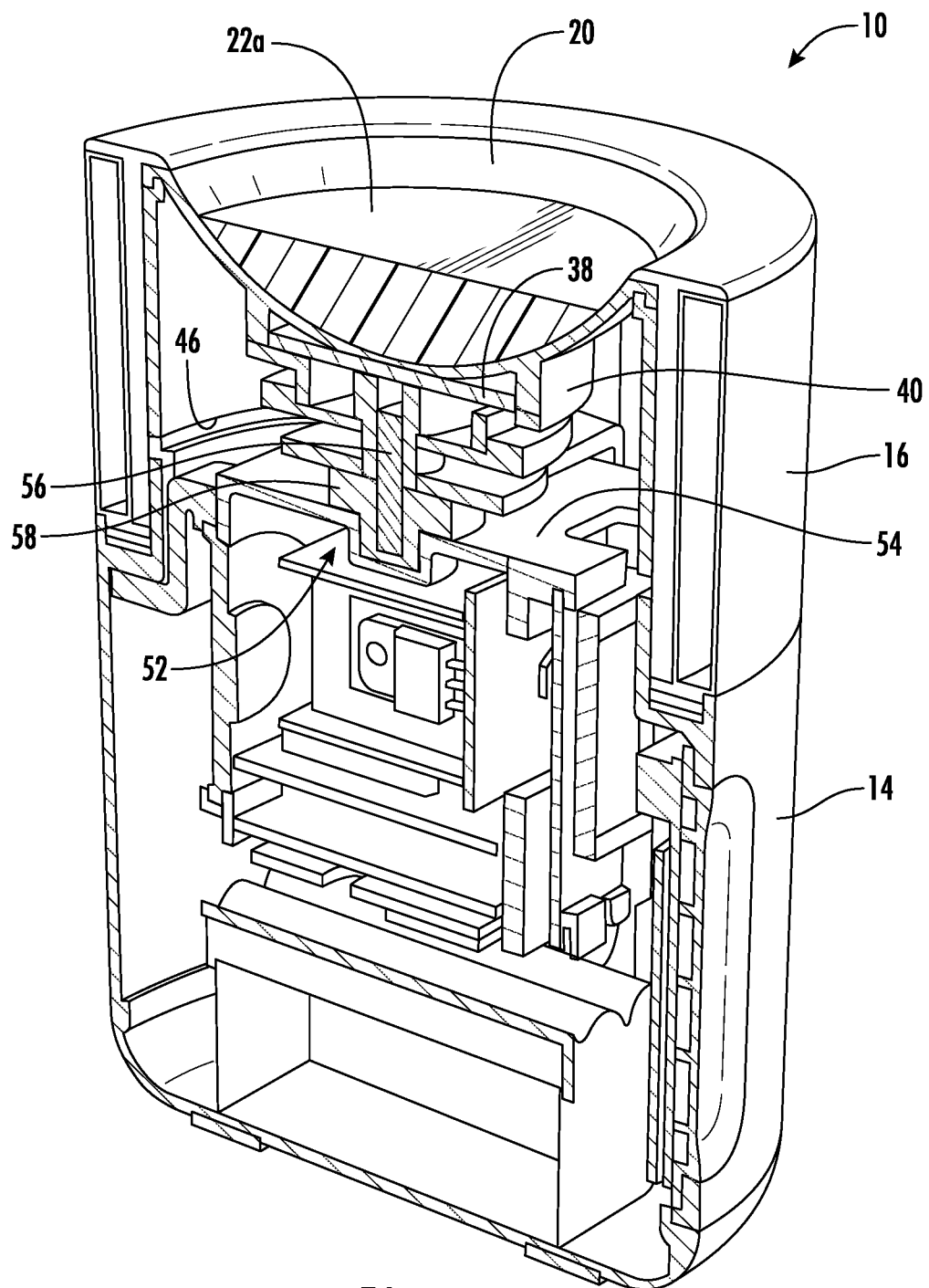
FIGS. 5A and 5B are various views of another embodiment of the wax melter apparatus constructed in accordance with the present disclosure.
Figure 5B:
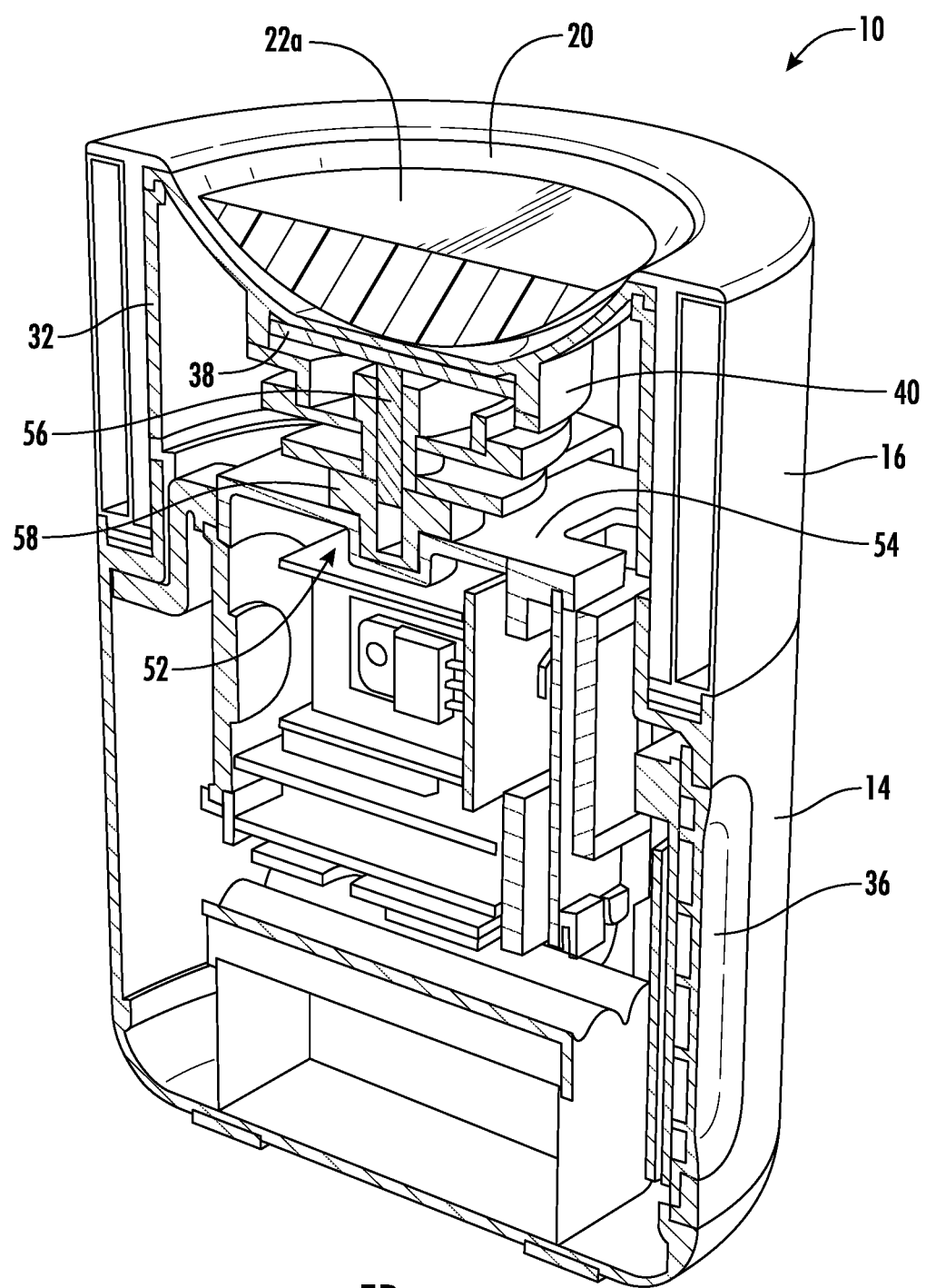

In another embodiment shown in FIGS. 5A and 5B, the wax removal mechanism can include a linear actuator 52 disposed between a support platform 54. When it is desirous for the cooled and hardened wax 22a to be removed from the flexible dish 20, the linear actuator 52 can be initiated and the rod 56 of the linear actuator can extend from the base 58 of the linear actuator 52 and engage the ejection apparatus 40. The engagement of the ejection apparatus 40 by the parts of the linear actuator causes the ejection apparatus 40 to engage the flexible dish 20 and distort the shape of the flexible dish 20. The distortion of the shape of the flexible dish 20 causes the cooled and hardened wax 22a to be unstuck from the flexible dish 20. The linear actuator 52 can be set up to operate via a button disposed in the housing 12 of the wax melter apparatus 10.

From the above description, it is clear that the present disclosure is well-adapted to carry out the objectives and to attain the advantages mentioned herein as well as those inherent in the disclosure. While presently preferred embodiments have been described herein, it will be understood that numerous changes may be made which will readily suggest themselves to those skilled in the art and which are accomplished within the spirit of the disclosure and claims.

What is claimed is:

1. A wax melter apparatus, the wax melter apparatus comprising:
   a housing having a base portion and an upper portion wherein the upper portion of the housing is unthreaded with respect to the base portion and is rotatable relative to the base portion;
   a heating element to provide heat to melt wax; and
   a dish supported by the housing, the dish receives wax to be melted and is distortable to allow cooled and hardened wax to be easily removed.

2. The apparatus of claim 1 wherein the base portion includes a top side with an LED ring disposed thereon.

3. The apparatus of claim 2 wherein the upper portion of the housing has a sleeve cavity created by an inner sleeve and an outer sleeve and the LED ring is disposed between the inner sleeve and the outer sleeve of the upper portion.

4. The apparatus of claim 2 further comprising a dimmer pad disposed in the base portion, the dimmer pad controls the brightness of the LED ring and turns the wax melter apparatus on and off.

5. The apparatus of claim 1 wherein the dish is made of a silicon based material.

6. The apparatus of claim 1 wherein rotation of the upper portion of the housing relative to the base portion causes distortion of the dish and eases removal of cooled and hardened wax from the dish.

7. The apparatus of claim 1 further comprising a wax removal mechanism that includes a rod member and an arm member wherein rotation of the arm member drives the rod member upward into the heating element or an ejection apparatus that supports the heating element to force the heating element into the dish to distort the dish and dislodge the cooled and hardened wax out of dish.

8. The apparatus of claim 7 wherein the rod member is threadably engaged with an opening in the arm member.

9. The apparatus of claim 8 wherein the upper portion is rotatable relative to the body portion of the housing, the upper portion includes an outer sleeve and an inner sleeve that includes at least one horizontal slot therein that one end of the arm member extends therethrough wherein rotation of the upper portion rotates the arm member to move the rod member up and down relative to the dish.

10. The apparatus of claim 9 wherein the inner sleeve includes a second horizontal slot that a second end of the arm member can engage to facilitate rotation of the arm member.

11. The apparatus of claim 1 wherein various functions of the wax melter apparatus can be operable with a mobile application.

12. The apparatus of claim 1 wherein the wax melter apparatus includes a wax life preservation feature that causes the heating element to toggle between different temperatures to cause the wax life to last longer and reintroduce scent from the wax into living spaces where the wax melter apparatus is used.

13. The apparatus of claim 1 wherein various functions of the wax melter apparatus is operated by voice command of a user of the wax melter apparatus.

14. A wax melter apparatus, the wax melter apparatus comprising:

a housing having a base portion and an upper portion wherein the base portion includes a top side with an LED ring disposed thereon, the upper portion of the housing has a sleeve cavity created by an inner sleeve and an outer sleeve and the LED ring is disposed between the inner sleeve and the outer sleeve of the upper portion;

a heating element to provide heat to melt wax; and a dish supported by the housing, the dish receives wax to be melted and is distortable to allow cooled and hardened wax to be easily removed.

15. The apparatus of claim 14 further comprising a dimmer pad disposed in the base portion, the dimmer pad controls the brightness of the LED ring and turns the wax melter apparatus on and off.

16. The apparatus of claim 14 wherein the flexible dish is made of a silicon based material.

17. The apparatus of claim 14 wherein various functions of the wax melter apparatus can be operable with a mobile application.

18. The apparatus of claim 14 wherein the wax melter apparatus includes a wax life preservation feature that causes the heating element to toggle between different temperatures to cause the wax life to last longer and reintroduce scent from the wax into living spaces where the wax melter apparatus is used.

19. The apparatus of claim 14 wherein the outer sleeve of the upper portion is transparent.

20. A wax melter apparatus, the wax melter apparatus comprising:

a housing;

a heating element to provide heat to melt wax;

a dish supported by the housing, the dish receives wax to be melted and can be distorted to allow cooled and hardened wax to be easily removed; and a wax removal mechanism that includes a linear actuator wherein a rod of the linear actuator forces the heating element into the dish to distort the dish and dislodge the cooled and hardened wax out of the dish.

21. The apparatus of claim 20 wherein the linear actuator is disposed on a support platform.

22. The apparatus of claim 20 wherein the linear actuator includes a base the rod extends in and out of.

* * * * *